United States Patent [19]

Krishnamurthy et al.

[11] Patent Number: 5,185,139
[45] Date of Patent: Feb. 9, 1993

[54] CARBON DIOXIDE PRODUCTION FROM COMBUSTION EXHAUST GASES WITH NITROGEN AND ARGON BY-PRODUCT RECOVERY

[75] Inventors: Ramachandran Krishnamurthy, Piscataway; Mark J. Andrecovich, Somerville, both of N.J.

[73] Assignee: The BOC Group, Inc., New Providence, N.J.

[21] Appl. No.: 850,535

[22] Filed: Mar. 13, 1992

Related U.S. Application Data

[62] Division of Ser. No. 560,625, Jul. 31, 1990, Pat. No. 5,100,635.

[51] Int. Cl.⁵ .................. C01C 1/04; C07C 273/04
[52] U.S. Cl. ........................... 423/359; 564/69
[58] Field of Search ................. 423/359; 564/69

[56] References Cited

U.S. PATENT DOCUMENTS

| | | | |
|---|---|---|---|
| 2,545,778 | 3/1951 | Haringhuizen | 423/359 |
| 3,498,067 | 3/1970 | Ranke | 62/24 |
| 3,872,025 | 3/1975 | Singleton | 423/359 |
| 4,255,406 | 3/1981 | Isalski et al. | 423/359 |
| 4,371,381 | 2/1983 | Schuftan | 62/24 |
| 4,595,404 | 6/1986 | Ozero et al. | 62/24 |
| 4,613,492 | 9/1986 | Winter | 423/359 |
| 4,704,146 | 11/1987 | Markbretter et al. | 62/28 |
| 4,759,786 | 7/1988 | Atkinson et al. | 62/24 |
| 5,068,058 | 11/1991 | Bushinsky et al. | 423/359 |
| 5,069,891 | 12/1991 | Bendix et al. | 423/359 |

Primary Examiner—Wayne Langel
Attorney, Agent, or Firm—Coleman R. Reap; Larry Cassett

[57] ABSTRACT

The present invention is directed to a method for producing carbon dioxide and nitrogen from combustion exhaust gas containing less than about 10% oxygen by weight which comprises the steps of (a) treating the exhaust gas to remove particulate matter, (b) compressing the exhaust gas to a pressure in the range from about 25 psia to about 200 psia, (c) purifying the exhaust gas to remove trace contaminants, (d) separating the exhaust gas to produce a carbon dioxide rich fraction and a nitrogen rich fraction, (e) liquifying the carbon dioxide rich fraction and distilling off volatile contaminants to produce pure carbon dioxide, (f) purifying the nitrogen rich fraction to remove contaminants, and (g) cryogenically fractionally distilling the nitrogen rich fraction to produce pure nitrogen. In another embodiment, the invention is directed to a method for producing carbon dioxide, nitrogen, and argon from a combustion exhaust gas. The combustion exhaust gas in the present invention may be obtained from an ammonia plant reformer furnace and the nitrogen produced may be employed as a synthesis gas in the ammonia reactor.

4 Claims, 3 Drawing Sheets

CARBON DIOXIDE PRODUCTION FROM COMBUSTION EXHAUST GASES WITH NITROGEN AND ARGON BY-PRODUCT RECOVERY

This is a division, of application Ser. No. 07/560,625, filed Jul. 31, 1990, now U.S. Pat. No. 5,100,635.

BACKGROUND OF HE INVENTION

1. Field of the Invention

The present invention is directed to a method for producing carbon dioxide, nitrogen, and optionally argon, from a combustion exhaust gas. More particularly, the present invention is directed to a method for separating carbon dioxide from an oxygen depleted combustion exhaust gas to produce a feed gas enriched in nitrogen and argon.

2. Description of the Prior Art

The commercial preparation of carbon dioxide and nitrogen is well known in the art. Carbon dioxide is normally produced as a by-product from chemical processes for producing ammonia, hydrogen, ethanol, ethylene oxide, and gasoline, as well as in fermentation reactions and carbonate decompositions. Nitrogen is generally produced by separation from air.

The preparation of carbon dioxide generally involves the steps of crude gas generation, purification and separation, compression and liquefaction, drying, and rectification distillation.

Generation of crude carbon dioxide involves the combustion of liquid fuels such as fuel oil, or solid fuels such as anthracites, coke, charcoal, and the like, with excess air to promote complete oxidation of the fuel and to provide a carbon dioxide rich combustion exhaust gas.

Purification of the combustion exhaust gas generally involves several separate treatments to provide a gas having high purity. These purification treatments include washing, absorption, adsorption, desorption, and the removal of reducing substances. Washing generally involves a water absorption shower (water wash) to remove solids (soot, carried off ashes, etc.) and at the same time to cool the combustion gases. Various scrubbing solutions are generally employed to remove contaminants and to reduce the components in the combustion gas mixture to carbon dioxide, nitrogen, and oxygen. The combustion exhaust gas may also be passed through a tower containing a recirculating oxidizing solution such as potassium permanganate to remove traces of organic impurities carried with the gas.

The washed and scrubbed combustion gas is then separated to obtain a carbon dioxide rich fraction. In one separation method, the combustion gas mixture is circulated through a counter-current shower of an absorbing solution such as potassium carbonate, monoethanol-amine, and the like. Carbon dioxide can be desorbed by heating the carbon dioxide saturated solution to a temperature above 100° C. In another separation method, the combustion mixture is separated by selectively adsorbing the carbon dioxide on a zeolite bed in a pressure swing adsorption system.

The purified and separated carbon dioxide is then compressed to a pressure in the range from about 230 psia to about 400 psia, dried by contacting the gas with a regenerable desiccant, and liquified by lowering the temperature of the gas. Finally, a rectification distillation step eliminates the small amount of nitrogen, oxygen, and argon to provide carbon dioxide having a purity of about 99.9% by volume.

The most common methods for separating nitrogen from air are cryogenic fractional distillation, inert gas generation (combustion of natural gas or propane in air), and pressure swing adsorption.

In cryogenic fractional distillation, air is compressed to about 100 psi and cooled in a reversing heat exchanger against outgoing nitrogen product gas and waste gas. Water, carbon dioxide, and hydrocarbons in the air are removed by condensation in the reversing heat exchanger. Alternatively, water, carbon dioxide, and hydrocarbons can be removed by passing air through a zeolite bed. The zeolite bed can be regenerated by passing heated nitrogen waste gas through the bed. The air is fed through a cold end gel trap where remaining small quantities of hydrocarbons and carbon dioxide are removed. The clean air is cooled further in a sub-cooler and is fed into a distillation column where the air is liquefied and separated into a high purity nitrogen product gas fraction and a waste gas fraction containing about 38% oxygen by weight. Both gas fractions are warmed to ambient temperature by passing the fractions through the sub-cooler and reversing heat exchanger.

In an inert gas generator, natural gas or propane is burned with air and the products of combustion are removed leaving purified nitrogen. The combustion of natural gas and air is controlled to provide a specific air to gas ratio in the burner to obtain essentially complete combustion. The combustion gas contains nitrogen, carbon dioxide, water vapor, and small amounts of carbon monoxide and hydrogen. Gases leaving the combustion chamber are cooled in a surface condenser to remove water. The gases then flow to a refrigerant dryer where the dew point is reduced to 4° C. Pure nitrogen product gas is then obtained by passing the gas through a molecular sieve bed in a pressure swing adsorption apparatus to remove carbon dioxide and any remaining water vapor.

In a pressure swing adsorption system (PSA), air is passed at an elevated pressure through a bed of an adsorbent material which selectively adsorbs oxygen. Nitrogen product gas is then withdrawn from the bed. The adsorption bed may be regenerated by reducing the pressure of the bed.

Issued to Weir et al., U.S. Pat. No. 3,493,339, discloses a method for producing carbon dioxide and separating argon which comprises combusting a carbonaceous material in a mixture of argon and oxygen and separating the combustion products to obtain carbon dioxide and argon.

Issued to Fuderer, U.S. Pat. No. 4,414,191, discloses a pressure swing adsorption method for purifying hydrogen for ammonia synthesis. Nitrogen at elevated pressure is used as the purge gas in the pressure swing adsorption separation and the nitrogen in the purified gas is employed in the ammonia synthesis stream.

Issued to Mercader et al., U.S. Pat. No. 4,797,141 discloses a method for obtaining carbon dioxide and nitrogen from the oxygen rich exhaust gas of an internal combustion engine or turbine. The method comprises the steps of cooling the exhaust gas by separating carbon dioxide from the cooled gas by absorbing the carbon dioxide ir .n alkaline solution, recovering the carbon dioxide by liberating the gas from the carbonated solution, compressing and liquifying the carbon dioxide, recovering the nitrogen by purifying the gas to remove contaminants, and compressing and liquifying the nitrogen.

While the above methods provide improvements in the production of carbon dioxide, none of these methods are entirely satisfactory. Conventional sources for producing carbon dioxide are carbon dioxide rich gases such as waste gases from ammonia, hydrogen, ethanol, and ethylene oxide plants These carbon dioxide sources are not always available or are not always reliable especially at locations of high carbon dioxide demand. Other common problems with the production of carbon dioxide are low product yield and energy inefficient separation methods. Conventional gas generation methods do not teach the preparation of food grade carbon dioxide as well as pure nitrogen and argon from combustion exhaust gases. Hence there is a need for an improved method for producing carbon dioxide. The present invention provides such an improved method and also provides an improved method for producing nitrogen and argon as by-products.

SUMMARY OF THE INVENTION

The present invention is directed to a method for producing carbon dioxide and nitrogen from combustion exhaust gas containing less than about 10% oxygen by weight which comprises the steps of (a) treating the exhaust gas to remove particulate matter, (b) compressing the exhaust gas to a pressure in the range from about 25 psia to about 200 psia, (c) purifying the exhaust gas to remove trace contaminants, (d) separating the exhaust gas to produce a carbon dioxide rich fraction and a nitrogen rich fraction, (e) liquifying the carbon dioxide rich fraction and distilling off volatile contaminants to produce pure carbon dioxide, (f) purifying the nitrogen rich fraction to remove contaminants, and (g) cryogenically fractionally distilling the nitrogen rich fraction to produce pure nitrogen. In another embodiment, the invention is directed to a method for producing carbon dioxide, nitrogen, and argon from a combustion exhaust gas. The combustion exhaust gas in the present invention may be obtained from an ammonia plant reforming furnace and the nitrogen produced may be employed as a synthesis gas in the ammonia reactor.

DETAILED DESCRIPTION OF THE INVENTION

Applicants have found that the production of carbon dioxide from a combustion exhaust gas (stack gas) containing less than about 10% oxygen by weight provides a method which efficiently and economically yields enriched carbon dioxide in high purity. After removal of trace contaminants from the oxygen depleted gas, liquid carbon dioxide is produced by bulk separation, liquefaction, and distillation of volatile impurities. Nitrogen, and optionally argon, are then recovered from the carbon dioxide depleted gas as by-products by cryogenic fractional distillation. The reduced oxygen concentration in the combustion exhaust gas provides process flexibility and capital cost reduction.

After carbon dioxide is separated from the stack gas, the concentration of nitrogen and argon in the stack gas is significantly higher than the concentration in air, the conventional source of these gases. This higher nitrogen and argon concentration is the result of oxygen being consumed in the combustion process. Separation of nitrogen and argon as by-products from the carbon dioxide depleted gas results in a significant reduction in energy (about 40%) compared to production from air separation. The present method provides an opportunity for reducing the cost for manufacturing liquid carbon dioxide and makes combustion exhaust gas a viable and attractive carbon dioxide source.

The gaseous nitrogen product obtained by the present method may be used as a synthesis gas or as an inert gas at the chemical plant which provides the combustion exhaust gas, such as a hydrogen plant or a refinery. Alternatively, the nitrogen product may be liquefied for distribution to other locations. The reduction in feedstream cost and distribution cost also offset the cost of bulk separation required to concentrate the relatively low carbon dioxide content of the combustion exhaust gas and the processing cost to remove trace contaminants such as nitrogen oxides ($NO_x$) and sulfur oxides ($SO_x$). Conversion of contaminants in the combustion exhaust gas to an easily disposable form and separation and recovery of the components also provides an efficient and attractive option to meet clean air regulations and environmental control.

In a preferred embodiment, the recovery of combustion exhaust gas from an ammonia plant reforming furnace is integrated with the synthesis process in the ammonia plant. A conventional method for producing ammonia is based on the primary steam reforming of natural gas or other hydrocarbon gas followed by secondary reforming with air to provide a hydrogen and nitrogen synthesis gas mixture. Contaminants such as carbon monoxide are removed by shift conversion (conversion of carbon monoxide with steam to form additional hydrogen and carbon dioxide) and contaminants such as carbon dioxide are removed by absorption in amines or other alkaline solvents. Carbon monoxide and carbon dioxide are also removed by methane formation (conversion of trace carbon monoxide and carbon dioxide to methane). The purified hydrogen and nitrogen synthesis gas mixture is then fed into the ammonia synthesis reactor.

A more recent method for producing ammonia is based on the production of pure hydrogen synthesis gas by steam reforming and on the production of pure nitrogen synthesis gas by separation of air. The production of hydrogen gas consists of steam reforming, carbon monoxide shift conversion and multiple bed pressure swing adsorption purification.

In a preferred embodiment, hydrogen gas is produced by steam reforming, shift conversion and pressure swing adsorption purification and is mixed with nitrogen gas recovered from the carbon dioxide depleted combustion exhaust from the ammonia plant steam reformer furnace. The hydrogen and nitrogen synthesis gas mixture reacts in the ammonia plant synthesis reactor to form ammonia. Furthermore, the carbon dioxide separated form the stack gas in the reforming step can be combined with the ammonia product gas in a urea plant to yield urea. Accordingly, the present method can provide pure nitrogen synthesis gas and carbon dioxide synthesis gas to yield product ammonia and urea at lower energy costs than conventional technologies.

Ammonia production processes and hydrogen production processes are disclosed in more detail in "Ammonia and Synthesis Gas: Recent and Energy Saving Processes", Edited by F. J. Brykowski, Chemical Technology Review No. 193, Energy Technology Review No. 68, Published by Noyes Data Corporation, Park Ridge, New Jersey, 1981, which disclosure is incorporated herein by reference.

In accord with the present invention, the method for producing carbon dioxide and nitrogen from combustion exhaust gas containing less than about 10% oxygen by weight comprises the steps of (a) treating the exhaust gas to remove particulate matter, (b) compressing the exhaust gas to a pressure in the range from about 25 psia to about 200 psia, (c) purifying the exhaust gas to remove trace contaminants, (d) separating the exhaust gas to produce a carbon dioxide rich fraction and a nitrogen rich fraction, (e) liquifying the carbon dioxide rich fraction and distilling off volatile contaminants to produce pure carbon dioxide, (f) purifying the nitrogen rich fraction to remove contaminants, and (g) cryogenically fractionally distilling the nitrogen rich fraction to produce pure nitrogen.

The combustion exhaust gas in the present invention is a combustion gas containing less than about 10% oxygen, preferably from about 1.5% to about 6% oxygen, and more preferably from about 1.5% to about 3% oxygen, by weight. The combustion preferably takes place in a fired heater (steam boiler) under approximately stoichiometric conditions, and moderation of the combustion can be achieved by recycle of some of the reaction products. A 10% excess of air to fuel is normally used in a fired heater to ensure complete combustion of the fuel and this air to fuel ratio results in approximately 2% oxygen concentration by weight in the stack gas.

Fuel such as natural gas, methane, coke, coal, fuel oil, or similar carbon-containing compounds may be combusted with air. The fuel supply may also be waste or exhaust gases from other sources. For example, in a combined cycle power plant, a gas engine or turbine may be initially used and the exhaust gas from the engine is further combusted in a fired heater with supplementary fuel to generate steam. The combustion exhaust gas may be obtained from a number of sources such as a power plant, cement and lime plants, and chemical plants such as ammonia plants and hydrogen plants. Chemical plant waste gases from refinery fluid catalytic cracking unit regeneration gases and combustion exhaust gas from incinerators may also be used.

In general, combustion gases from internal combustion engines or turbines are not suitable in the present invention because such exhaust gases contain high amounts of oxygen making the gas separation uneconomical. Typically a combustion engine uses 70% to 300% excess air to ensure complete combustion of the fuel and to prevent the engine or turbine from overheating during the combustion process. This level of excess air means that the oxygen concentration in the exhaust gas will be very high, typically about 17%. Because there is no substantial reduction in the oxygen concentration in the exhaust gas of an engine compared to the oxygen concentration in air (about 20%), there is no appreciable energy or capital cost savings advantage for producing nitrogen from the carbon dioxide depleted exhaust gas from an engine compared to the conventional production of nitrogen from air.

The method for producing carbon dioxide, nitrogen, and argon from a combustion exhaust gas can be better understood by reference to the figures in which like numerals refer to like parts of the invention throughout the figures. Although the present invention is described and illustrated in connection with preferred embodiments, applicants intend that modifications and variations may be used without departing from the spirit of the present invention.

Figure 1:
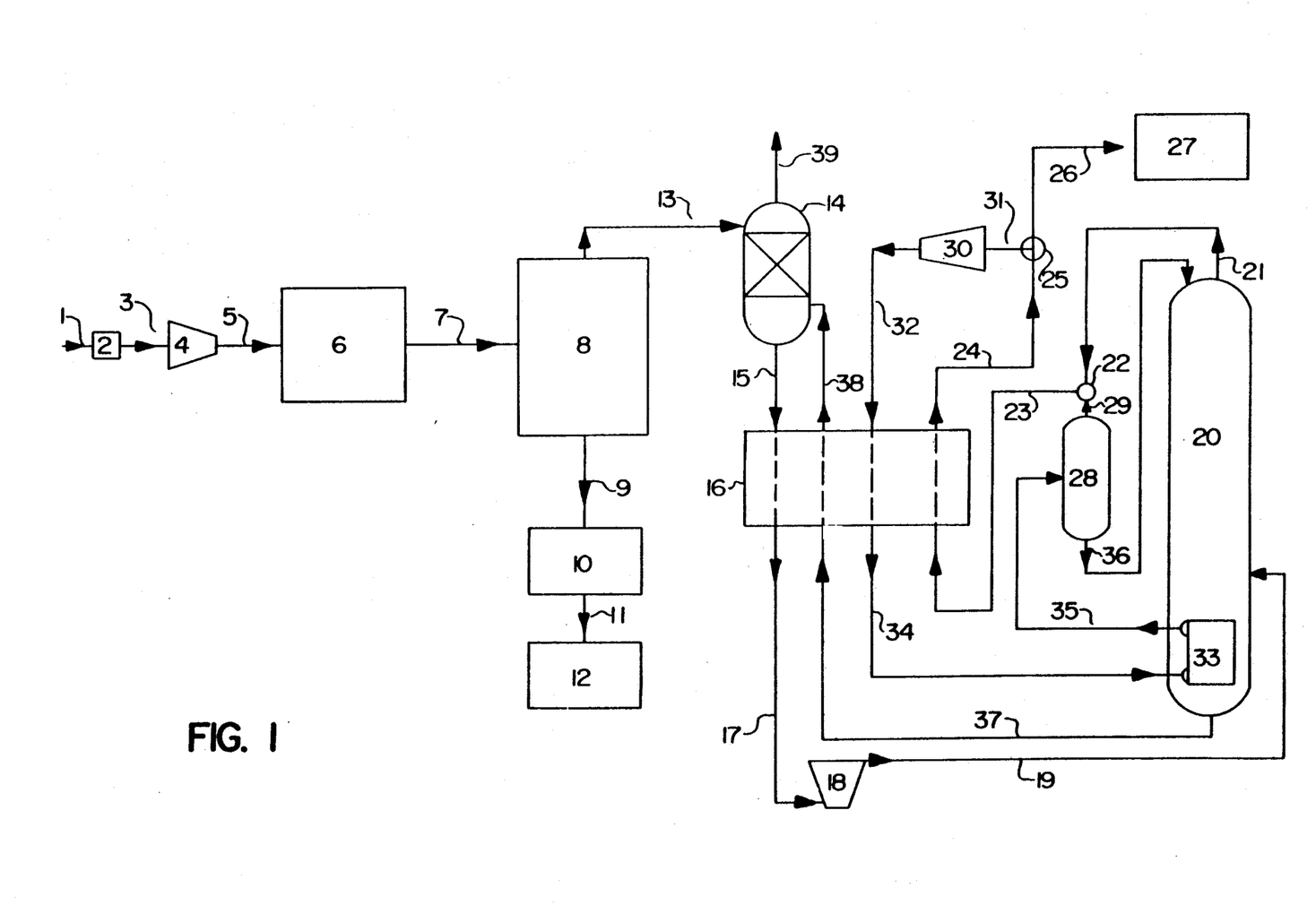
FIG. 1 is a schematic process flow diagram illustrating a method for the co-production of carbon dioxide and nitrogen according to the method of the present invention.

Referring to FIG. 1, combustion exhaust gas (stack gas, combustion gas, exhaust gas, feed gas, waste gas) is fed through gas feed conduit 1 to pre-purification unit 2 to remove particulate matter from the combustion exhaust gas. Pre-purification unit 2 may be a washing column wherein combustion gas is admitted from the bottom of the unit and a water absorption shower is administered to the gas from the top of the unit to remove solids (soot, carried off ashes, etc.). The washing column may at the same time cool the gas and remove sulfur anhydrides derived from sulfur contained in the fuel. Heat obtained from the combustion gas may be used to preheat the fuel gas in the fired heater.

The pre-purified combustion exhaust gas is then fed through gas feed conduit 3 to compressor 4. Compressor 4 compresses the combustion gas to the separation pressure. In general, the combustion exhaust gas is compressed to a separation pressure in the range from about 25 psia to about 200 psia, preferably from about 25 psia to about 120 psia, and more preferably from about 40 psia to about 100 psia.

The compressed combustion exhaust gas is then fed through gas feed conduit 5 to purification unit 6 where trace contaminants such as nitrogen oxides, sulfur oxides, and water are removed. For example, nitrogen oxides ($NO_x$, $NO$, $NO_2$) may be removed by treating the feed gas with ammonia and a selective catalyst (commercially available, for example, from Norton Company, Ohio) to convert the nitrogen oxides to nitrogen and water. Sulfur oxides ($SO_x$, $SO_2$, $SO_3$) may be removed by treating the feed gas with conventional flue gas desulfurization techniques such as alkali scrubbing. Other methods to remove nitrogen oxides and sulfur oxides include moving bed adsorption on activated carbon (Bergbau-Forschung process) and cyanuric acid treatment (RAPRENOx process developed by Sandia National Laboratories), respectively. Potassium permanganate scrubbing may also be included in the purification to reduce trace contaminants such as $NO_x$ to the desired level. The presence of nitrogen oxides and sulfur oxides in the combustion exhaust gas should be reduced to less than about 1 ppm to meet food grade specifications for liquid carbon dioxide products. Levels of carbon monoxide in the exhaust gas at concentrations higher than ambient can be removed by catalytic oxidative conversion to carbon dioxide. Water vapor can be removed, for example, by passing the feed gas through a tower containing a regenerable desiccant such as silica gel, alumina, or zeolite. Silica gel may be periodically re enerated by passing dry nitrogen heated to a temperature above 100° C. through the tower.

The purified combustion exhaust gas is then passed through gas feed conduit 7 to separation unit 8 to separate the gas to produce a carbon dioxide rich fraction and a nitrogen rich fraction. The separation of the feed gas can be carried out by any conventional method.

In one embodiment, the combustion exhaust gas may be circulated through carbon dioxide absorption columns (alkaline solutions such as monoethanolamine, potash, etc.) wherein carbon dioxide is absorbed to form a carbonated solution and nitrogen and the remaining gases pass though the column. The carbonate solution can be regenerated by passing steam or fluid at a temperature of about 125° C. through the carbonated solution. In a preferred embodiment, the combustion exhaust gas is separated in a pressure swing apparatus into a carbon dioxide rich stream and a nitrogen rich stream.

The carbon dioxide rich fraction from separation unit 8 is then fed through gas feed conduit 9 to liquefaction unit 10 wherein the carbon dioxide is liquified and the volatile contaminants are removed by distillation to produce pure carbon dioxide. Liquid carbon dioxide is produced by conventional processing steps that include compressing the gas to a pressure between about 230 psia and about 400 psia and cooling the gas to a temperature between about −8° F. and about −50° F. The more volatile impurities are removed from the liquid carbon dioxide by distillation. Pure carbon dioxide is then vented from liquefaction unit 10 through feed conduit 11 to carbon dioxide product reservoir 12.

The nitrogen rich fraction from separation unit 8 is then fed through gas feed conduit 13 to nitrogen purification unit 14 wherein the nitrogen fraction is purified to remove trace contaminants. The nitrogen rich fraction from the bulk carbon dioxide separation in separation unit 8 typically contains about 96% nitrogen, about 1.2% argon, and about 2.8% oxygen, by weight. Preferably, the nitrogen rich fraction is purified by passing the gas through a bed of zeolite molecular sieves to remove trace contaminants such as carbon dioxide.

Pure nitrogen gas is then generated by cryogenic fractional distillation. The nitrogen rich fraction from nitrogen purification unit 14 is fed through gas feed conduit 15 to heat exchanger 16 where the feed gas is cooled to close to its liquefaction point (with cooling energy derived from the outgoing product gas stream). Cooled nitrogen gas from heat exchanger 16 is fed through gas feed conduit 17 to feed expander 18 where the nitrogen gas is further cooled and partially liquified (typically from about 10% to about 15% of the nitrogen fraction is liquified). Cooled nitrogen gas from feed expander 18 is fed through gas feed conduit 19 to nitrogen generator 20 where pure nitrogen is cryogenically fractionally distilled from oxygen and argon. Pure nitrogen product gas passes from nitrogen generator 20 through gas feed conduit 21, gas mixing union 22, and gas feed conduit 23 to heat exchanger 16 where the product gas is brought to ambient temperature. Cooling energy from the pure nitrogen product gas is passed to heat exchanger 16 for cooling feed gas from nitrogen purification unit 14. Warmed product gas is then passed from heat exchanger 16 through gas feed conduit 24, gas splitting union 25, and gas feed conduit 26 to nitrogen product reservoir 27. Gas feed conduits 21 and 23 are connected by gas mixing union 22. Gas mixing union 22 is also connected to flash pot 28 via gas feed conduit 29. Gas feed conduits 24 and 26 are connected by gas splitting union 25. Gas splitting union 25 is also connected to nitrogen cycle compressor 30 via gas feed conduit 31.

A portion of the nitrogen product gas passes from gas feed conduit 24, gas splitting union 25, and gas feed conduit 31 to nitrogen cycle compressor 30 to supply the refrigeration loop. Nitrogen cycle compressor 30 compresses the nitrogen product gas into nitrogen refrigeration fluid. The nitrogen refrigeration fluid is cooled and partially liquified by passage to heat exchanger 16 via gas feed conduit 32. The cooled nitrogen refrigeration fluid then passes to reboiler 33 via gas feed conduit 34. Partially liquified nitrogen refrigeration fluid in reboiler 33 accepts cooling energy from reboiler 33. After being substantially liquified, the nitrogen refrigeration fluid from reboiler 33 passes to flash pot 28 via feed conduit 35. Flash pot 28 expands the nitrogen refrigeration fluid to a lower pressure to subcool the refrigeration fluid. Flash pot 28 separates liquified nitrogen refrigeration fluid and gaseous nitrogen refrigeration fluid. Liquified nitrogen refrigeration fluid from flash pot 28 is returned as reflux to nitrogen generator 20 via feed conduit 36. Gaseous nitrogen refrigeration fluid from flash pot 28 is passed through gas feed conduit 29 and gas mixing union 22 to join pure nitrogen product in gas feed conduit 23. After passage through heat exchanger 16 and gas feed conduit 24, the product gas is again split at gas splitting union 25 between nitrogen product reservoir 27 and nitrogen cycle compressor 30 to pass into the refrigeration loop.

Oxygen rich product gas in nitrogen generator 20 is vented from the bottom of nitrogen generator 20 via gas feed conduit 37 to heat exchanger 16 to provide cooling energy to the heat exchanger. The warmed gas from heat exchanger 16 is passed to nitrogen purification unit 14 (zeolite bed) via gas feed conduit 38 to be used as regeneration gas. Optionally, the regeneration gas may be further warmed by a heater prior to use in purification unit 14. After regeneration of nitrogen purification unit 14, the oxygen rich waste gas is then vented from nitrogen purification unit 14 via gas feed conduit 39.

In another embodiment, the invention is directed at a method for producing carbon dioxide, and nitrogen and argon as by-products from combustion exhaust gas containing less than about 10% oxygen by weight. After carbon dioxide is separated from the stack gas, the concentration of nitrogen and argon in the stack gas is considerably higher than the concentration in air, the conventional source of these gases. Separation of nitrogen and argon as by-products from the carbon dioxide depleted gas results in a significant reduction in energy and cost for manufacturing liquid carbon dioxide. Furthermore, the product combination consisting of carbon dioxide, nitrogen, and argon may be more attractive for certain plant locations where production of oxygen is not in great demand.

Figure 2:
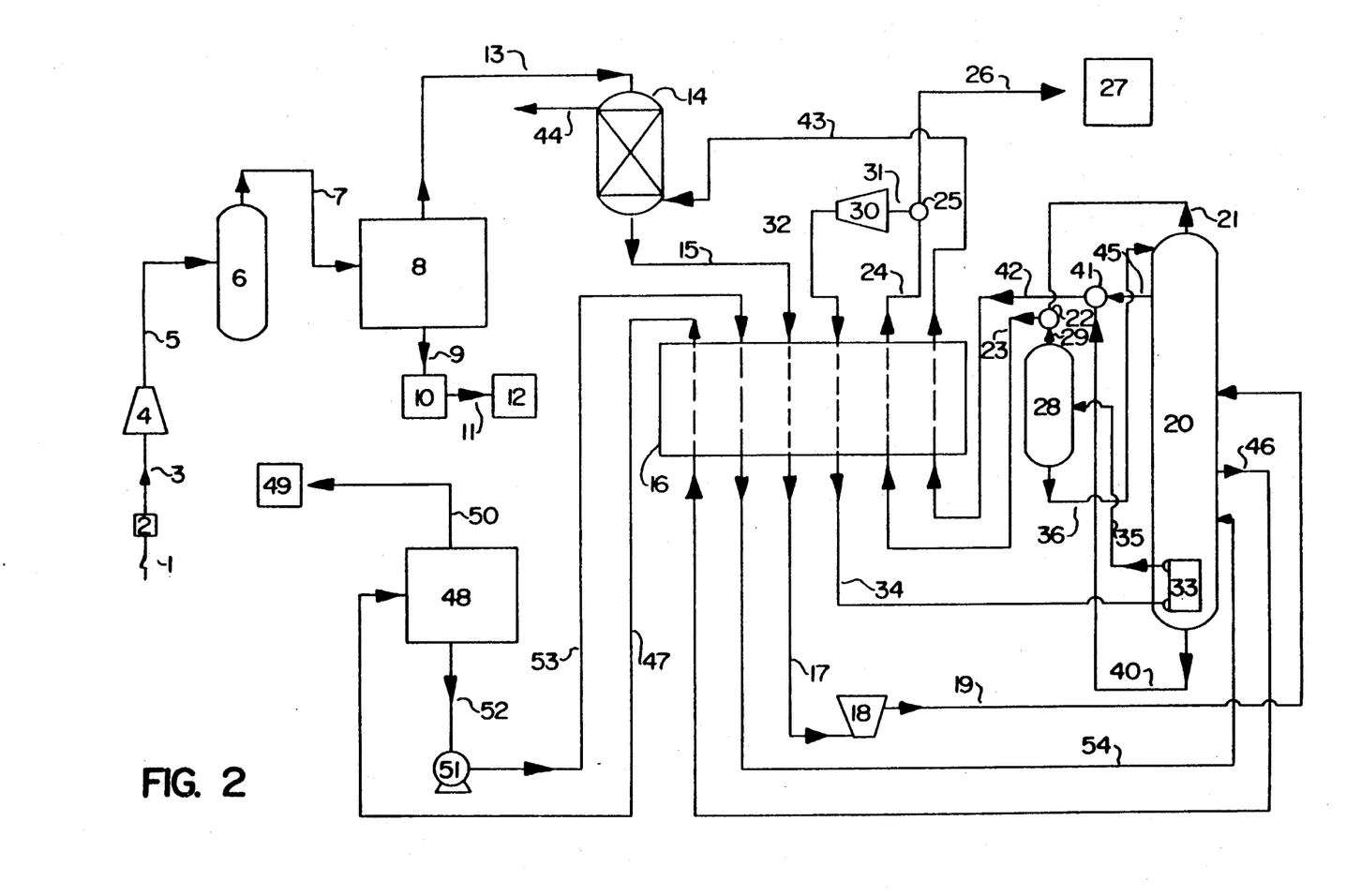
FIG. 2 is a schematic process flow diagram illustrating a method for the production of carbon dioxide, nitrogen, and argon according to the method of the present invention.

Referring to FIG. 2, the combustion exhaust gas is fed to pre-purification unit 2 to remove particulate matter from the combustion exhaust gas, as set out above for FIG. 1. The pre-purified combustion exhaust gas is then fed to compressor 4 which compresses the combustion gas to the separation pressure. The compressed combustion exhaust gas is then passed to purification unit 6 to remove trace contaminants. The purified gas is fed to separation unit 8 to separate the gas to produce a carbon dioxide rich fraction and a nitrogen rich fraction. The carbon dioxide rich fraction is then fed to liquefaction unit 10 wherein the carbon dioxide is liquified by conventional means and the volatile contaminants are removed by distillation to produce pure carbon dioxide. Pure carbon dioxide is fed to carbon dioxide product reservoir 12. The nitrogen rich fraction is then fed to nitrogen purification unit 14 wherein the nitrogen rich fraction (carbon dioxide depleted) is purified to remove trace contaminants such as carbon dioxide in a zeolite based adsorption purification system. The nitrogen rich fraction from nitrogen purification unit 14 is fed to heat exchanger 16 where the feed gas is cooled to close to its liquefaction point. Cooled nitrogen gas from heat exchanger 16 is fed to feed expander 18 where the nitrogen gas is partially liquified. Cooled nitrogen feed from feed expander 18 is fed to nitrogen generator 20 where pure nitrogen is fractionated from argon, as set out above for FIG. 1.

Nitrogen waste gas can be vented from nitrogen generator 20 through gas feed conduit 45 located near the top of nitrogen generator 20, gas mixing union 41, and gas feed conduit 42 to heat exchanger 16 and gas feed conduit 43 for regeneration of nitrogen purification unit 14 and venting through gas feed conduit 44. An argon rich fraction in nitrogen generator 20 is vented from the middle of nitrogen generator 20 via gas feed conduit 46 to heat exchanger 16 to warm the gas. Warmed argon rich fraction gas is then passed to argon generator 48 through gas feed conduit 47.

In one preferred embodiment, argon generator 48 is a pressure swing adsorption unit. Argon generator 48 separates the argon rich fraction into crude argon product and an oxygen rich fraction. Crude argon product from argon generator 48 is passed to argon product reservoir 49 via gas feed conduit 50. The oxygen rich fraction containing argon from argon generator 48 is passed to compressor 51 via gas feed conduit 52 to be compressed. Compressed oxygen rich fraction is then passed to heat exchanger 16 via gas feed conduit 53 to be cooled and then to nitrogen generator 20 via gas feed conduit 54 to recycle residual argon.

In another preferred embodiment, argon generator 48 is a second cryogenic distillation unit (not shown in FIG. 2). When argon generator 48 is a cryogenic distillation unit, the argon rich fraction gas is not warmed prior to passing the gas into argon generator 48 and the oxygen rich fraction withdrawn from argon generator 48 is not cooled prior to passing the fraction into nitrogen generator 20.

Pure nitrogen gas and crude argon (98+% argon and less than 2% oxygen, by weight) can be generated by employing two cryogenic distillation columns or one cryogenic distillation column and a pressure swing adsorption apparatus utilizing a carbon molecular sieve adsorbent. The first cryogenic distillation column fractionates the feed gas into a pure nitrogen product of desired purity and an oxygen (and argon) rich fraction. When two cryogenic distillation columns are employed, the argon in the feed gas is separated with the oxygen rich fraction in the first cryogenic distillation column and is fractionated in the second cryogenic distillation column as a crude argon product. When one cryogenic distillation column and a carbon molecular sieve (CMS) pressure swing adsorption apparatus are employed, an argon rich fraction is withdrawn from the cryogenic distillation column and separated in the carbon molecular sieve pressure swing adsorption apparatus into a crude argon product and an oxygen rich waste fraction. The oxygen rich waste fraction is recycled to the cryogenic distillation column. The reflux for the cryogenic column(s) is provided by a recirculating nitrogen stream which acts as a heat pump to recover the cooling energy from the reboiler. Additional cooling energy is generated by expansion of the cooled feed gas or a portion of the compressed and cooled recirculating nitrogen.

In a preferred embodiment, the invention is directed at a method for producing carbon dioxide, nitrogen, and argon from a combustion exhaust gas containing less than about 10% oxygen by weight which comprises the steps of:

(a) treating the exhaust gas to remove particulate matter;
(b) compressing the exhaust gas to a pressure in the range from about 25 psia to about 200 psia;
(c) purifying the exhaust gas to remove trace contaminants;
(d) separating the exhaust gas to produce a carbon dioxide rich fraction and a nitrogen and argon rich fraction;
(e) liquifying the carbon dioxide rich fraction and distilling off volatile contaminants to produce pure carbon dioxide;
(f) purifying the nitrogen and argon rich fraction to remove contaminants;
(g) cryogenically fractionally distilling the nitrogen and argon rich fraction to produce pure nitrogen and an argon rich fraction; and
(h) purifying the argon rich fraction to produce pure argon.

In another embodiment, the invention is directed at an improved method for the production of ammonia. Nitrogen gas, recovered from the carbon dioxide depleted combustion exhaust gas from the ammonia plant steam reformer furnace according to the method of the present invention, can be utilized in the ammonia plant as a synthesis gas with hydrogen synthesis gas produced by steam reforming, shift conversion and pressure swing adsorption purification.

Steam reforming, in the hydrogen production process, consists of treating a hydrocarbon feed gas with steam in a catalytic steam reactor (reformer) which consists of a number of tubes placed in a furnace at a temperature in the range from about 1400° F. to about 1700° F. The reforming reactions which occur when methane is used as the hydrocarbon feed gas are set out below.

$$CH_4 H_2O = CO + 3H_2$$

$$CH_4 + 2H_2O = CO_2 + 4H_2$$

$$CO + H_2O = CO_2 H_2$$

The hydrogen rich gas mixture exiting the steam reformer consists of an equilibrium mixture of hydrogen, steam, carbon monoxide, carbon dioxide, and small amounts of unreacted methane. The reforming reactions are endothermic and require heat. Therefore, some hydrocarbon and process waste gases are burned in air in the reformer furnace to provide the endothermic heat for the reforming reactions as well to preheat the feed and steam mixture.

Heat is extracted from the hot synthesis gases by cooling the gases with boiler feed water to a temperature of about 750° F. in a process boiler. The boiler feed water is converted to steam.

The cooled hydrogen rich gas is then treated in a shift converter to aid in the conversion of carbon monoxide into additional hydrogen and carbon dioxide. The shift conversion reaction is favored at lower temperatures such as about 750° F. compared to the higher temperatures in the steam reformer.

The gases exiting the shift reactor are cooled in a process cooler to ambient temperature. The heat extracted from the gases is used to heat make-up water to produce boiler feed water for the process boiler. Condensate is also removed from the synthesis gas and is cycled into the make-up water to provide the feed to generate boiler feed water.

After being cooled, the shift reactor gases are then treated in a hydrogen pressure swing adsorption purification unit to produce pure hydrogen gas for ammonia synthesis. The pressure swing adsorption system usually 4 and 12 adsorption vessels and operates on a process sequence consisting of the following steps: (i) adsorption to adsorb impurities on the bed and release pure hydrogen, (ii) several stages of pressure equalization to conserve hydrogen in the void gas at the end of the adsorption step, (iii) depressurization and purge with a portion of the hydrogen product gas to regenerate the bed and to remove impurities, and (iv) repressurization of the adsorption bed using pressure equalization gas and finally product hydrogen. The gas mixture released in step (iii) which is referred to as hydrogen pressure swing adsorption purge gas is cycled to the reformer furnace for burning to recover fuel value.

Figure 3:
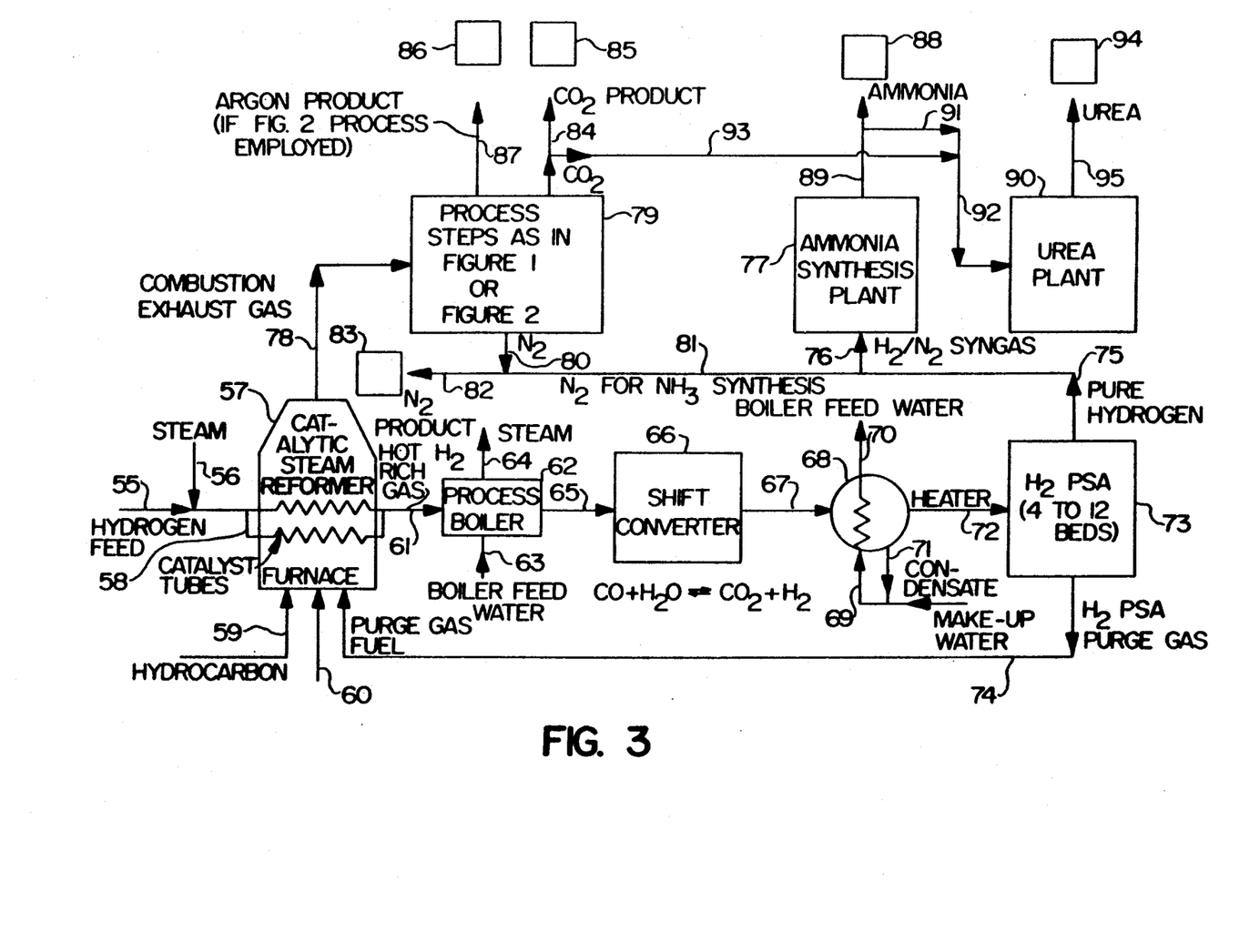
FIG. 3 is a schematic drawing of an apparatus suitable for integrating the recovery of the production of carbon dioxide, nitrogen, and argon from the combustion exhaust gas of an ammonia reforming furnace into an ammonia synthesis plant.

Referring to FIG. 3, hydrocarbon feed gas is fed through gas conduit 55 and steam is fed through gas conduit 56 to catalytic steam reformer (reactor) 57 containing catalyst tubes 58. Hydrocarbon fuel is fed through gas conduit 59 and air is fed through gas conduit 60 to the furnace in catalytic steam reformer 57. A hot hydrogen rich gas mixture exits catalytic steam reformer 57 through gas conduit 61 and passes into process boiler 62 where heat is extracted from the hot synthesis gases in process boiler 62. Boiler feed water is introduced into process boiler 62 via conduit 63 and steam is removed from process boiler 62 via conduit 64. The cooled hydrogen rich gas is then passed into shift converter 66 via gas conduit 65 where carbon monoxide is converted into hydrogen and carbon dioxide. The gases exiting shift converter 66 are passed via gas conduit 67 into process cooler 68 where heat is extracted from the gases in process cooler 68 and condensate is removed. Make-up feed water is introduced into process cooler 68 via conduit 69 and heated boiler feed water is removed from process cooler 68 via conduit 70. Condensate removed from the synthesis gas is then cycled into the make-up water via conduit 71 to provide the feed water to generate boiler feed water.

The cooled shift reactor exit gases are withdrawn from process cooler 68 and passed via gas conduit 72 to hydrogen pressure swing adsorption purification unit 73 to produce pure hydrogen gas. Pressure swing adsorption purification unit 73 may contain between 4 and 12 adsorption vessels. Hydrogen pressure swing adsorption purge gas mixture is vented from hydrogen pressure swing adsorption purification unit 73 via gas conduit 74 and cycled into the furnace of catalytic steam reformer 57 to be burned as purge gas to recover fuel value. Pure hydrogen synthesis gas is then vented from hydrogen pressure swing adsorption purification unit 73 via gas conduits 75 and 76 to ammonia synthesis plant 77.

Combustion exhaust gas from catalytic steam reformer 57 is vented through gas conduit 78 to separation unit 79 wherein the combustion exhaust gas is separated into carbon dioxide, nitrogen, and argon rich fractions according to the method of the present invention. Separation unit 79 may be a separation unit as described above in FIG. 1 or in FIG. 2. Pure nitrogen synthesis gas is vented from separation unit 79 via gas conduits 80, 81, and 76 to ammonia synthesis plant 77. The pure nitrogen synthesis gas from separation unit 79 and pure hydrogen synthesis gas from hydrogen pressure swing adsorption purification unit 73 are employed in ammonia synthesis plant 77 to yield ammonia according to the method of the present invention.

Pure nitrogen gas may also be vented from separation unit 79 to nitrogen product reservoir 83 via gas conduits 80 and 82. Pure carbon dioxide gas is vented from separation unit 79 to carbon dioxide product reservoir 85 via gas conduit 84. Pure argon gas is vented from separation unit 79 to argon product reservoir 86 via gas conduit 87. Ammonia product gas from ammonia synthesis plant 77 is vented to ammonia product reservoir 88 via gas conduit 89.

Ammonia product gas from ammonia synthesis plant 77 may also be vented to urea synthesis plant 90 via gas conduits 91 and 92. Carbon dioxide gas from separation unit 79 may also be vented to urea synthesis plant 90 via gas conduits 93 and 92. The pure ammonia product gas from ammonia synthesis plant 77 and pure carbon dioxide gas from separation unit 79 are employed in urea synthesis plant 90 to prepare urea according to the method of the present invention. Urea product from urea synthesis plant 90 is vented to urea product reservoir 94 via gas conduit 95.

In a preferred embodiment, the invention is directed at an improved method for the production of ammonia which comprises the steps of:

(a) steam reforming a hydrocarbon feed gas to produce a hydrogen-rich synthesis gas;

(b) purifying the hydrogen-rich synthesis gas to remove contaminants to produce pure hydrogen;

(c) burning a hydrocarbon fuel to supply heat for the steam reforming reaction of step (a) wherein the hydrocarbon burning produces a combustion exhaust gas containing less than about 10% oxygen by weight;

(d) treating the exhaust gas to remove particulate matter;

(e) compressing the exhaust gas to a pressure in the range from about 25 psia to about 200 psia;

(f) purifying the exhaust gas to remove trace contaminants;

(g) separating the exhaust gas to produce a carbon dioxide rich fraction and a nitrogen rich fraction;

(h) liquifying the carbon dioxide rich fraction and distilling off volatile contaminants to produce pure carbon dioxide;

(i) purifying the nitrogen rich fraction to remove contaminants;

(j) cryogenically fractionally distilling the nitrogen rich fraction to produce pure nitrogen; and (k) passing the pure nitrogen from step (j) and the pure hydrogen from step (b) into an ammonia synthesis reactor.

In another preferred embodiment, the pure carbon dioxide from step (h) is combined with the ammonia from step (k) in a urea reactor to produce urea.

As set out above, carbon dioxide and argon are preferably separated by pressure swing adsorption. In a pressure swing adsorption system (PSA), a gaseous mixture is passed at an elevated pressure through a bed of an adsorbent material which selectively adsorbs one or more of the components of the gaseous mixture. Product gas, enriched in the unadsorbed gaseous component(s), is then withdrawn from the bed. The adsorption bed may be regenerated by reducing the pressure of the bed.

The term "gaseous mixture", as used herein, refers to a gaseous mixture, such as air, primarily comprised of two or more components having different molecular size. The term "enriched gas" refers to a gas comprised of the component(s) of the gaseous mixture relatively unadsorbed after passage of the gaseous mixture through the adsorbent bed. The enriched gas generally must meet a predetermined purity level, for example, from about 90% to about 99%, in the unadsorbed component(s). The term "lean gas" refers to a gas exiting from the adsorption bed that fails to meet the predetermined purity level set for the enriched gas. When the strongly adsorbed component is a desired product, a co-current depressurization step (co-current with respect to direction of the feed gas) and a co-current purge step of the strongly adsorbed component are added.

The selectivity of the adsorbent material in the bed for a gaseous component is generally governed by the volume of the pore size and the distribution of that pore size in the adsorbent. Gaseous molecules with a kinetic diameter less than, or equal to, the pore size of the adsorbent are adsorbed and retained in the adsorbent while gaseous molecules with a diameter larger than the pore size of the adsorbent pass through the adsorbent. The adsorbent thus sieves the gaseous molecules according to their molecular size. The adsorbent may also separate molecules according to their different rates of diffusion in the pores of the adsorbent.

Zeolite molecular adsorbents adsorb gaseous molecules with some dependence upon crystalline size. In general, adsorption into zeolite is fast and equilibrium is reached typically in a few seconds. The sieving action of zeolite is generally dependent upon the difference in the equilibrium adsorption of the different components of the gaseous mixture. When air is separated by a zeolite adsorbent, nitrogen is preferentially adsorbed over oxygen and the pressure swing adsorption method may be employed to produce an oxygen enriched product. When carbon dioxide, nitrogen, and argon are separated by a zeolite adsorbent, carbon dioxide is the adsorbed component and nitrogen and argon ar the unadsorbed components.

The sieving action of carbon molecular sieves is generally not dependent upon differences in equilibrium adsorption but rather by differences in the rate of adsorption of the different components of the gaseous mixture. When air is separated by carbon molecular sieves, oxygen is preferentially adsorbed over nitrogen and the pressure swing adsorption method may be employed to produce a nitrogen enriched product. When argon and oxygen are separated by carbon molecular sieves, argon is the unadsorbed component and oxygen is the adsorbed component.

As a gaseous mixture travels through a bed of adsorbent, the adsorbable gaseous components of the mixture enter and fill the pores of the adsorbent. After a period of time, the composition of the gas exiting the bed of adsorbent is essentially the same as the composition entering the bed. This period of time is known as the break-through point. At some time prior to this break-through point, the adsorbent bed must be regenerated. Regeneration involves stopping the flow of gaseous mixture through the bed and purging the bed of the adsorbed components generally by venting the bed to atmospheric or subatmospheric pressure.

A pressure swing adsorption system generally employs two adsorbent beds operated on cycles which are sequenced to be out of phase with one another by 180° so that when one bed is in the adsorption step, the other bed is in the regeneration step. The two adsorption beds may be connected in series or in parallel. In a serial arrangement, the gas exiting the outlet end of the first bed enters the inlet end of the second bed. In a parallel arrangement, the gaseous mixture enters the inlet end of all beds comprising the system. Generally, a serial arrangement of beds is preferred for obtaining a high purity gas product and a parallel arrangement of beds is preferred for purifying a large quantity of a gaseous mixture in a short time cycle.

As used herein, the term "adsorption bed" refers either to a single bed or a serial arrangement of two beds. The inlet end of a single bed system is the inlet end of the single bed while the inlet end of the two bed system (arranged in series) is the inlet end of the first bed in the system. The outlet end of a single bed system is the outlet end of the single bed and the outlet end of the two bed system (arranged in series) is the outlet end of the second bed in the system. By using two adsorption beds in parallel in a system and by cycling (alternating) between the adsorption beds, product gas can be obtained continuously.

Between the adsorption step and the regeneration step, the pressure in the two adsorption beds is generally equalized by connecting the inlet ends of the two beds together and the outlet ends of the two beds together. During pressure equalization, the gas within the pores of the adsorption bed which has just completed its adsorption step (under high pressure) flows into the adsorption bed which has just completed its regeneration step (under low pressure) because of the pressure differential which exists between the two beds. This pressure equalization step improves the yield of the product gas because the gas within the pores of the bed which has just completed its adsorption step has already been enriched. It is also common to employ ore than one pressure equalization step. When a number of pressure qualizations steps are employed, it is common to have ore than two beds in the adsorption system.

Gas separation by the pressure swing adsorption method is ore fully described in "Gas Separation by Adsorption Processes", Ralph T. Yang, Ed., Chapter 7, "Pressure Swing Adsorption: Principles and Processes" Buttersworth 1987, which reference is incorporate herein by reference.

Throughout this application, various publications have been referenced. The disclosures in these publications are incorporated herein by reference in order to more fully describe the state of the art.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. An improved method for the production of ammonia which comprises the steps of:
   (a) steam reforming a hydrocarbon feed gas to produce a hydrogen-rich synthesis gas;

(b) purifying the hydrogen-rich synthesis gas to remove contaminants to produce high purity hydrogen;

(c) burning a hydrocarbon fuel to supply heat for the steam reforming reaction of step (a) wherein the hydrocarbon burning produces a combustion exhaust gas containing less than about 10% oxygen, by weight;

(d) treating the exhaust gas to remove particulate matter;

(e) compressing the exhaust gas to a pressure in the range from about 25 psia to about 200 psia;

(f) purifying the exhaust gas to remove trace contaminants;

(g) separating the exhaust gas to produce a carbon dioxide rich fraction and a nitrogen rich fraction;

(h) liquefying the carbon dioxide rich fraction and distilling off components that are more volatile than carbon dioxide;

(i) purifying the nitrogen rich fraction to remove carbon dioxide;

(j) cryogenically fractionally distilling the nitrogen rich fraction to remove oxygen and argon therefrom; and (k) passing the nitrogen product from step (j) and the high purity hydrogen from step (b) into an ammonia plant synthesis reactor to produce ammonia.

2. The method according to claim 1, wherein the carbon dioxide product from step (h) is combined with the ammonia from step (k) in a urea reactor to produce urea.

3. The method according to claim 1, wherein the exhaust gas in step (g) is separated by pressure swing adsorption to produce a carbon dioxide-rich fraction and a nitrogen-rich fraction.

4. The method according to claim 1, wherein the nitrogen-rich fraction in step (i) is purified to remove contaminants by passing the nitrogen-rich fraction through a bed of zeolite molecular sieves.

* * * * *